Figure 1:
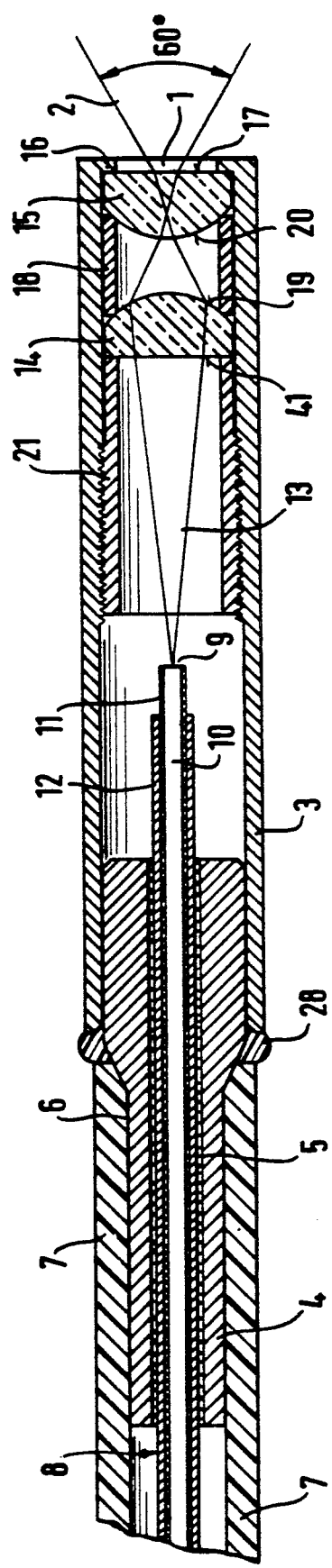

United States Patent [19]

Wagnières et al.

[11] Patent Number: 5,146,917
[45] Date of Patent: Sep. 15, 1992

[54] FIBRE-OPTIC APPARATUS FOR THE PHOTODYNAMIC TREATMENT OF TUMORS

[75] Inventors: Georges Wagnières, Lutry; Hubert van den Bergh, Goumoens-la-Ville; Philippe Monnier, Lausanne, all of Switzerland

[73] Assignee: Ciba-Geigy Corporation, Ardsley, N.Y.

[21] Appl. No.: 638,248

[22] Filed: Jan. 4, 1991

[30] Foreign Application Priority Data

Jan. 9, 1990 [CH] Switzerland .................. 59/907

[51] Int. Cl.⁵ .................................................. A61N 5/06
[52] U.S. Cl. .................................... 128/397; 128/395; 606/15; 606/17; 604/21
[58] Field of Search ................ 128/395, 397, 398; 606/7–18; 604/21

[56] References Cited

U.S. PATENT DOCUMENTS

| | | | |
|---|---|---|---|
| 4,017,150 | 4/1977 | Imai | 350/231 |
| 4,445,892 | 5/1984 | Hussein et al. | 606/18 |
| 4,551,129 | 11/1985 | Coleman et al. | 604/21 |
| 4,660,925 | 4/1987 | McCaughan, Jr. | 606/16 |
| 4,693,244 | 9/1987 | Daikuzon | 606/16 |
| 4,693,556 | 9/1987 | McCaughan, Jr. | 606/16 |
| 4,842,390 | 6/1989 | Sottini et al. | 606/7 |

FOREIGN PATENT DOCUMENTS 2154761 2/1985 United Kingdom .................. 606/16

*Primary Examiner*—David M. Shay
*Attorney, Agent, or Firm*—Wenderoth, Lind & Ponack

[57] ABSTRACT

A bronchoscope has a fibre-optic apparatus for the photodynamic treatment of tumors in the region of the furcate branches of the bronchi, the divergent pencil of rays (13), which emerges from the end face (9) of an optical fibre, striking a lens arrangement consisting of two microlenses (14,15) which, owing to the spherical aberration, deflect edge rays (23) in the divergent pencil of rays (13) of the optical fibre (8) in such a manner that a homogeneous sharp-edged emerging pencil of rays is formed.

6 Claims, 5 Drawing Sheets

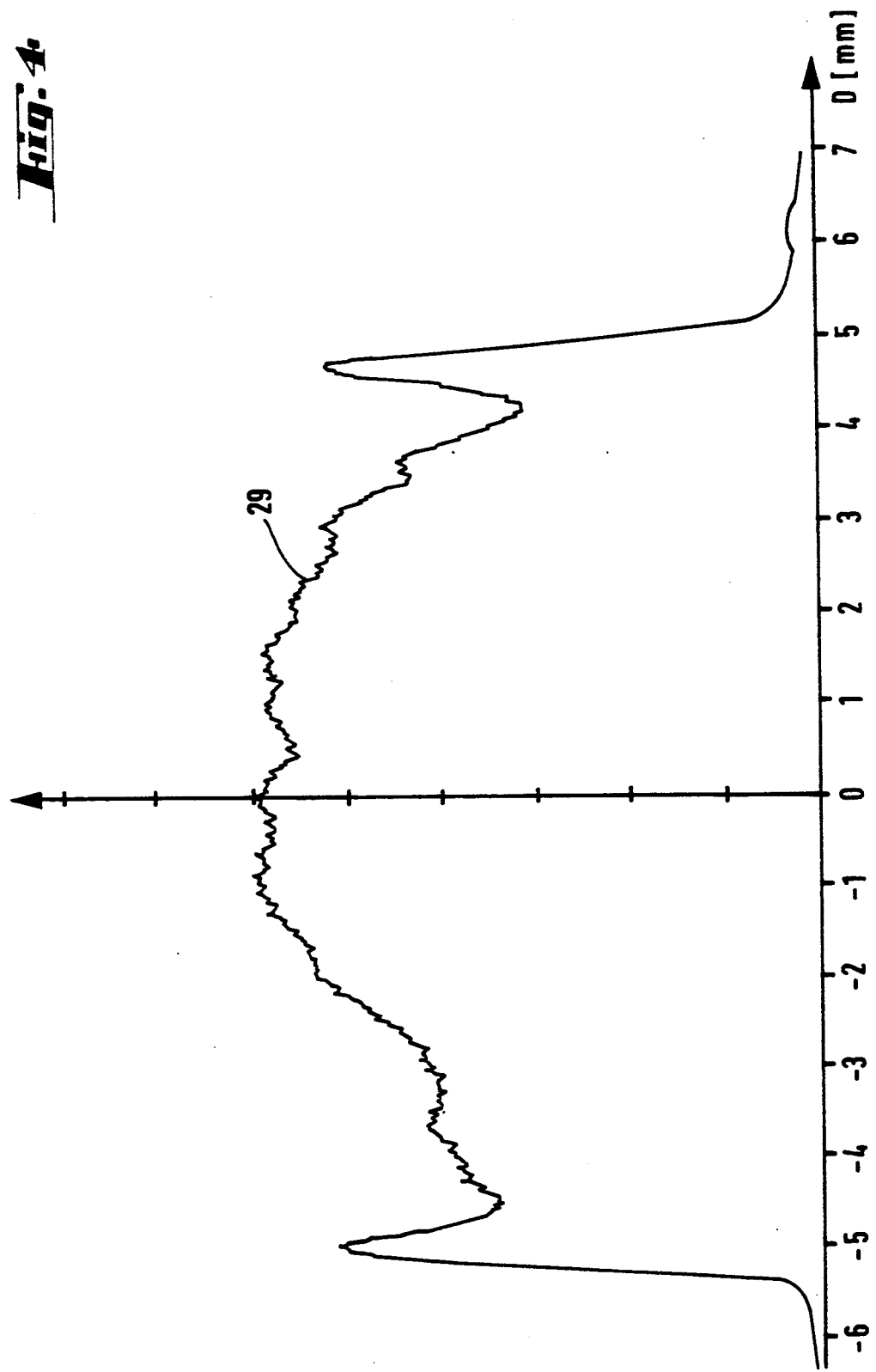

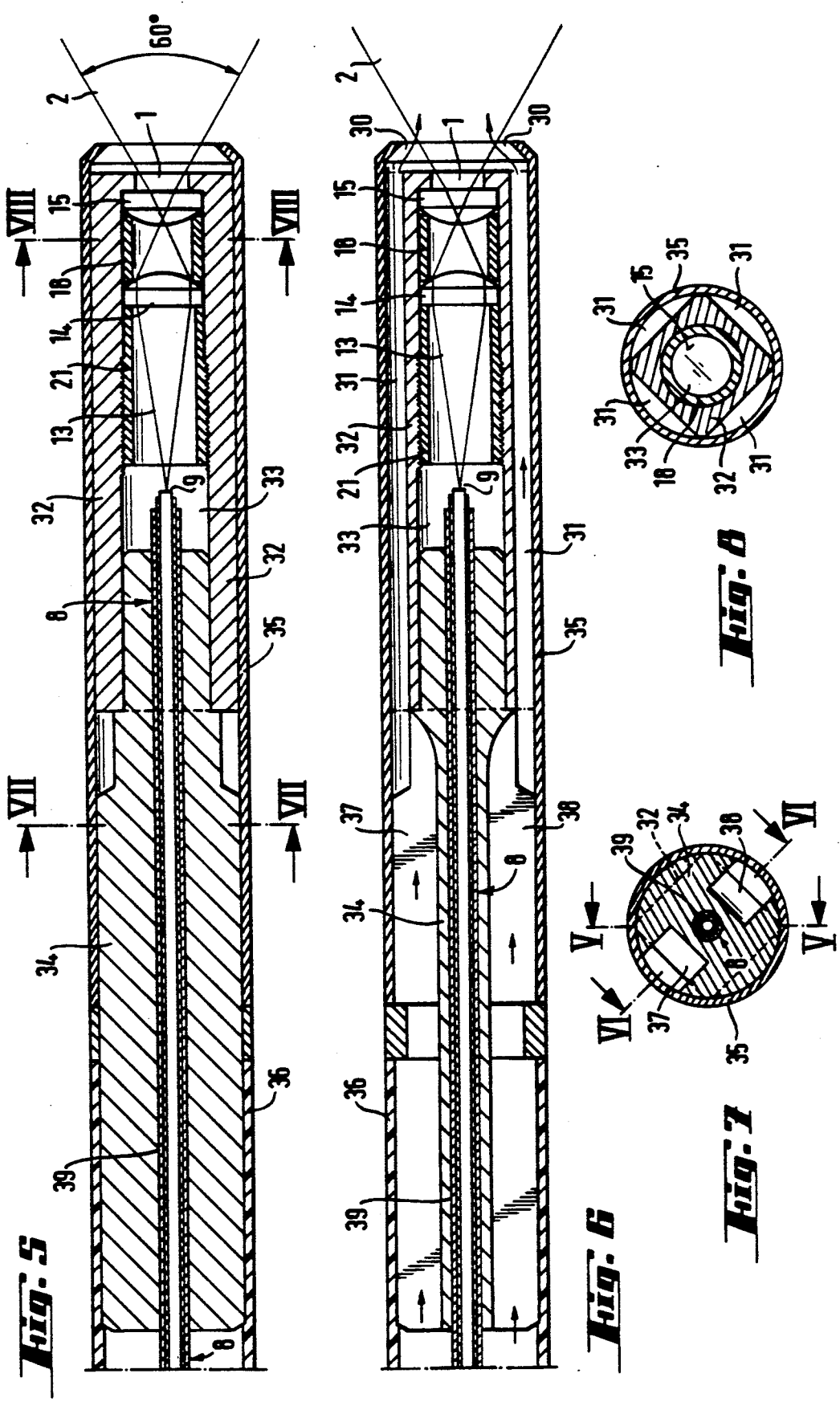

FIBRE-OPTIC APPARATUS FOR THE PHOTODYNAMIC TREATMENT OF TUMORS

The invention relates to a fibre-optic apparatus for the photodynamic treatment of tumours, especially in the respiratory system and the lungs of a patient, which apparatus has an optical fibre connected to a laser for conveying light to the site of the tumour.

A bronchoscope of that type is described in Chemistry in Britain, Vol. 22, No. 5, May 1986, Hubert van den Bergh, "Light and porphyrins in cancer therapy" and permits the detection and treatment of malignant lung tumours, especially on the furcate branches of the bronchi. Such treatment involves injecting a patient with porphyrin. After several days, the tumour tissue has absorbed considerably more of the dyestuff than has the healthy tissue. If the suspicious site is then irradiated, for example with a krypton laser connected to a quartz-fibre optical system, the cancer tissue is recognised by the red light emanating therefrom. In addition to this effect, which permits the detection of tumours, porphyrin has yet another advantageous property which is that it absorbs red light strongly, there being triggered in the diseased tissue a series of photochemical reactions which kill the tumour tissue, which contains the higher levels of porphyrin. The high-intensity red light required for that purpose can be conveyed to the tumour likewise by way of a quartz-fibre optical system, thereby selectively destroying the cancer cells in the course of such photodynamic therapy.

An optical wide-angle illuminating apparatus, for example for endoscopic use, is known from DE-OS 25 44 519. That apparatus does not, however, exploit the spherical aberration of lenses to light the illuminated surface homogeneously and with sharp edges. Rather, the pattern of intensity over the illuminated surface is bell-shaped, as shown in FIG. 5 of the Offenlegungsschrift. That apparatus is accordingly unsuitable, in photodynamic therapy, for sharp-edged illumination of the tissue surface to be irradiated.

Proceeding from that prior art, the problem of the invention is to provide a fibre-optic apparatus of the type mentioned at the beginning which permits the homogeneous and sharp-edged illumination of a tissue surface for the purpose of photodynamic treatment.

This problem is solved according to the invention in the case of a fibre-optic apparatus of the type mentioned at the beginning by arranging coaxially respect to the lightemitting end face of the fibre a pair of lenses that are so adjusted and have a spherical aberration such that the edge rays of the divergent pencil of rays emerging from the end face of the fibre are so greatly refracted by the first lens of the lens pair, owing to its spherical aberration, that, after traversing radially the central ray axis of the pair of lenses short of the focal point, they enter the surface of the second lens of the lens pair at a site lying diametrically opposite the site of emergence from the surface of the first lens, as a result of which the angle of divergence of the edge rays is reduced.

In an advantageous embodiment of the invention, the lenses of the lens pair are similar plano-convex microlenses, the focal length of which is smaller than their diameter and the facing convex sides of which are at a distance from one another that is smaller than the focal length of the microlenses.

The distance from the end face of the fibre to the flat surface of the first lens is a multiple of the focal length of the two microlenses. The pair of lenses is arranged near the front end of a lens tube in the rear end of which the optical fibre is secured.

According to a development of the invention, it is provided that the lens tube is surrounded by an air-supply tube, and between the lens tube and the air-supply tube there are arranged air ducts that open into air nozzles provided on the front end of the air-supply tube.

Further advantageous details and constructions can be found in the subsidiary claims and the description which follows.

Embodiments of the invention are described in detail hereinafter with reference to the drawings.

Figure 2:
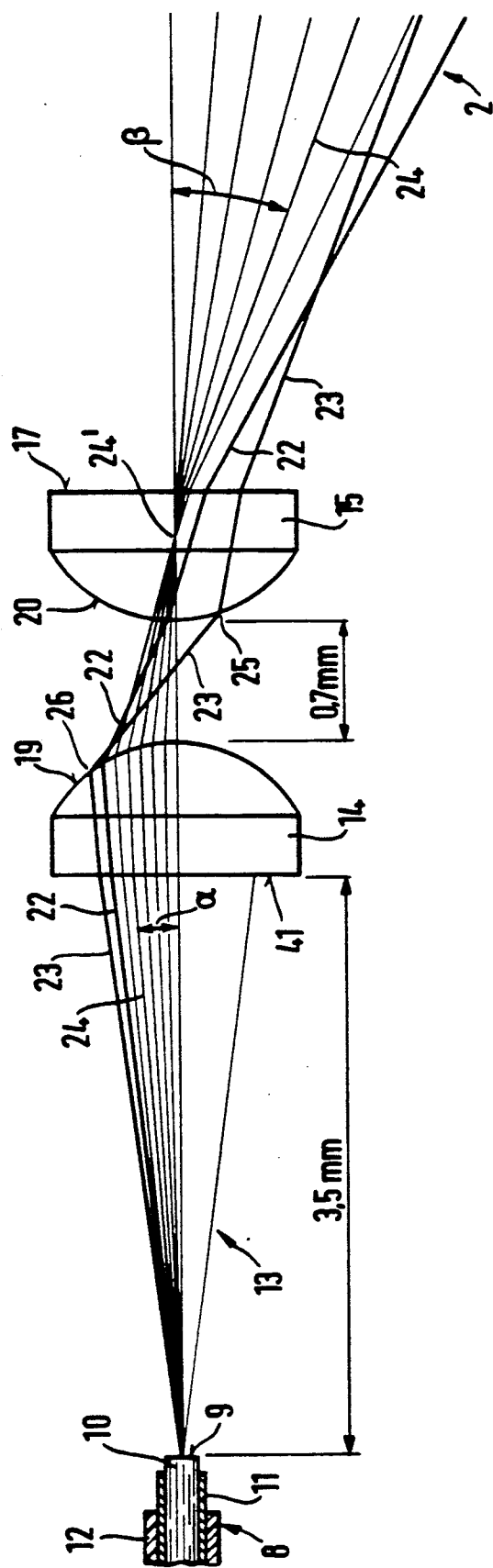
Figure 3:
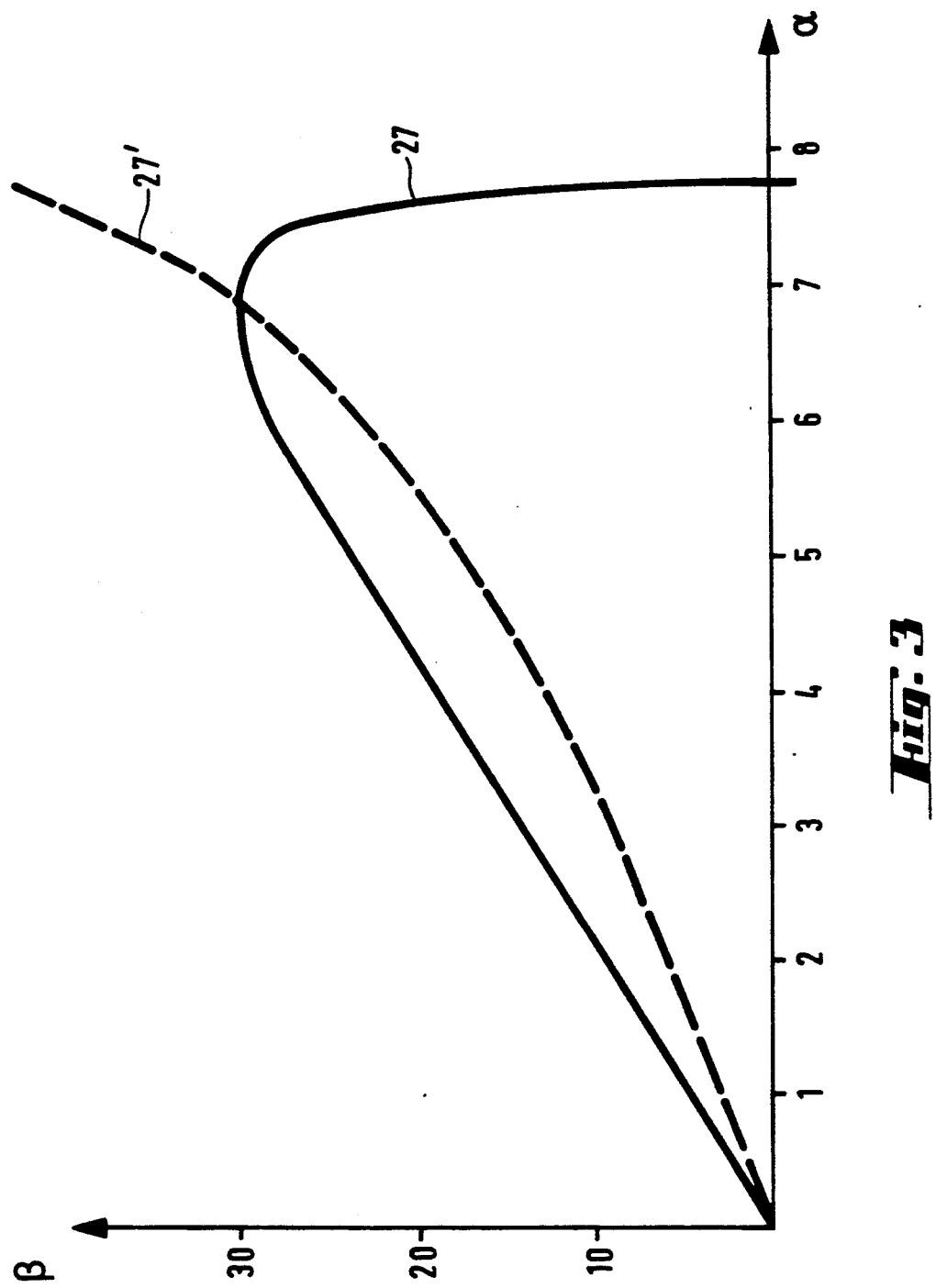

FIG. 1 shows a fibre-optic apparatus according to the invention having a microdiffuser emitting light in the axial direction, FIG. 2 is a diagrammatic view illustrating the path of rays between the end face of the optical fibre and the outlet of the microdiffuser, FIG. 3 shows the shape of the function of the angle of divergence of a ray at the outlet of the microdiffuser in dependence on the angle of entry into the first lens of the lens pair at the front end of the microdiffuser, FIG. 4 shows the shape of the intensity profile at a distance of 8 mm in front of the pair of lenses of the microdiffuser, FIG. 5 shows a longitudinal section through a second embodiment of a microdiffuser according to the invention having air nozzles at the front end, FIG. 6 shows the microdiffuser according to FIG. 5 in longitudinal section along a plane which, relative to the cutting plane in FIG. 5, has been rotated through 45 degrees about the longitudinal axis of the microdiffuser, FIG. 7 shows a cross-section through the microdiffuser along the line VII—VII in FIG. 5 and FIG. 8 shows a cross-section through the microdiffuser along the line VIII—VIII in FIG. 5.

FIG. 1 shows an axial or frontal microdiffuser which, at a distance of 8 mm in front of its outlet aperture 1, enables a disc-shaped surface having a diameter of approximately 10 mm to be illuminated with a high degree of edge-sharpness and homogeneity. The tissue illuminated by the light emerging from the outlet aperture 1 can accordingly be irradiated very selectively, owing to the sharp outline of the illuminated area, without also illuminating adjacent tissue in an undesired manner. In addition, the light energy in the cone 2 of emerging light is homogeneously distributed to a high degree, further homogenisation being caused by the illuminated tissue.

The frontal microdiffuser shown in section in FIG. 1 has as a housing a lens tube or refined steel tube 3 having an outside diameter of 2 mm and a length of 12 mm. Inserted in the left end, as seen in FIG. 1, of the refined steel tube 3 is a metal tube 4 through which the duct 5 extends. The portion of the metal tube 4 projecting from the left end of the refined steel tube 3 has a tapered portion 6 so that the outside diameter of the metal tube 4 is smaller outside the refined steel tube 3 and is approximately 1.1 mm.

Slipped onto the metal tube 4 is a plastics tube, especially a PTFE tube 7, the outside diameter of which is approximately 1.8 mm and the wall thickness of which is approximately 0.35 mm. An annular silicone seal 28 is arranged between the PTFE tube 7 and the refined steel tube 3 in the region of the tapered portion 6. The PTFE tube 7 serves to guide the refined steel tube 3, when the latter is passed through a patient's trachea, as far as the furcate branches of the patient's bronchi that are to be examined and treated.

Extending through the lumen of the PTFE tube 7 is an optical fibre 8 which is secured in the duct 5 of the metal tube 4 by means of an adhesive so that the end face 9 of the fibre 8 is fixed securely in position inside the refined steel tube 3 at the desired distance from the outlet aperture 1.

The optical fibre 8 has a fibre core 10, having a core diameter of 200 μm, which is surrounded by a cladding 11 having a diameter of 280 μm. A sheath 12 shown in FIG. 1 serves to protect the optical fibre 8 and to come into contact with the adhesive in the duct 5 of the metal tube 4.

In the case of photodynamic treatment of a lung tumour, red laser light is fed at a laser power of 500 mW and a maximum of 2 W into the feed-in end (not shown in FIG. 1) of the optical fibre 8. The light, which is present in many modes, is transmitted, starting from the laser, via a suitable optical connector arrangement and the optical fibre 8 through the PTFE tube 7 and finally passes through the metal tube 4 into the inner cavity of the refined steel tube 3 where it emerges from the end face 9 in the form of a divergent pencil of rays 13 with a characteristic angle of emergence of only 22 degrees with a Gaussian distribution.

The divergent pencil of rays 13 first strikes a first, for example plano-convex, microlens 14 and then a second, for example plano-convex, microlens 15. The microlenses 14, 15 form a pair of lenses and are so adjusted that the divergent pencil of rays 13, which has a low degree of edge-sharpness and is inhomogeneous, is sharpened at its edges and homogenised over its cross-section. In order to obtain a transmission of 75% instead of only 60% through the lens pair consisting of the microlenses 14, 15, the microlenses 14, 15 are coated with an anti-reflective layer of $MgF_2$.

As shown in FIG. 1, there is provided at the front end of the refined steel tube 3 a stop flange 16 which faces radially inwards and against which the flat side 17 of the second plano-convex microlens 15 rests. A brass ring 18 acts as a spacer between the second microlens 15 and the first microlens 14. FIG. 1 also shows how the first microlens 14 has its convex upper side 19 so orientated that the latter faces the convex upper side 20 of the second microlens 15. Pressing against the flat side 41 of the first microlens 14 is a brass tube 21 which is secured inside the refined steel tube 3 by means of a threaded portion in order to fix the lens pair, consisting of the microlenses 14 and 15, in the refined steel tube 3 at the spacing defined by the brass ring 18.

The lens pair consisting of the microlenses 14, 15 uses the spherical aberration of the lenses to ensure a homogeneous sharp-edged illuminated surface in the cone 2 of emerging light.

FIG. 2 shows a portion of the path of rays on an enlarged scale in order to illustrate the special adjustment and selection of the microlenses 14, 15.

Shown on the left in FIG. 2 is the optical fibre 8 having the fibre core 10, the cladding 11 and the sheath 12. The numerical aperture of the fibre is, for example, 0.21. The attenuation at 850 nm is less than 4 dB/km. The light of the divergent pencil of rays 13 emerging from the end face 9 is shown in FIG. 2 by a series of rays, the edge ray 22 and the outermost edge ray 23, which is indicated by a thicker line, being of particular importance for understanding the path of rays. A central ray 24 of the divergent pencil of rays 13 has the angle of divergence α, shown in FIG. 2, on entry into the first microlens 14 and the angle of emergence β after passing through the second microlens 15.

The plano-convex microlenses 14, 15 are lenses made of flint glass (La SF9) having a diameter of 1.5 mm and a focal length of 1 mm. The refractive index of the flint glass is 1.876 at a wavelength of 630 nm. Owing to their high degree of surface curvature, both microlenses 14, 15 are distinguished by a very strong spherical aberration which is exploited to homogenise and sharpen the cone 2 of emerging light. The greater the angle of divergence α, the greater is the spherical aberration. As can be seen from FIG. 2, the rays of the pencil of rays 13 having a small angle of divergence are deflected through the microlens 14 into a focal point 24' located in the body of the second microlens 15. These rays then form rays of the cone 2 of emerging light that are near the central axis.

Owing to the spherical aberration, however, the edge ray 22 is, as shown in FIG. 2, so greatly refracted that it passes through the central axis between the microlenses 14, 15 before the focal point 24'. When the angle of divergence α becomes as great as that of the outermost edge ray 23, the spherical aberration results in such a high degree of refraction that the refracted outermost edge ray 23 strikes the convex upper side 20 of the second microlens 15 at a site 25 that is diametrically opposite the site 26 where the refracted outermost edge ray 23 leaves the convex upper side 19 of the first microlens 14.

Owing to the orientation of the upper side 20 in the region of site 25, the outermost edge ray 23 is, in the manner shown in FIG. 2, not refracted away from the central axis between the microlenses 14, 15 but in the direction towards the central axis between the microlenses 14, 15 and is thus refracted towards the longitudinal axis of the frontal micro-diffuser. As a consequence, the outermost edge ray 23, after leaving the flat side 17 of the second microlens 15, has an angle of emergence β which is smaller than the angle of emergence β of other rays in the edge region having a smaller angle of divergence α, such as, for example, the edge ray 22.

This relationship is shown in FIG. 3 by the shape of a curve 27 which shows how, as the angle of divergence α increases, the angle of emergence β first increases in approximately linear manner and then falls sharply from an angle of slightly more than 7 degrees. A broken line 28 shows the angle dependence which results when, instead of the pair of lenses consisting of the microlenses 14, 15, a single lens having a spherical aberration is used.

FIG. 3, which shows only the positive branch of the function having a positive and negative divergence angle branch, illustrates how, in the cone 2 of emerging light, a maximum cone angle of approximately twice 30 degrees or 60 degrees is formed owing to the strong spherical aberration of the first microlens 14, which aberration is exploited in a special manner. The curve 27 shows the relationship in the case of rays emerging from the edge of the core of the optical fibre. The angle-dependent light distribution as a function of the angle of divergence α in the pencil of rays 13 relative to the longitudinal axis results in rays in the edge region assuming a maximum angle of emergence β or limit value angle of only approximately 30 degrees since the curve 27 does not continue to increase as does the function 28, which is shown by a broken line, but falls again from the limit value angle.

FIG. 4 shows an intensity profile with relative intensity units such as results when a light spot is produced at a distance of 8 mm in front of the second microlens 15. It can be gathered from the abscissa that the diameter of the light spot in the above-mentioned embodiment is approximately 10 mm, the intensity falling abruptly at the edge of the light spot or the illumination disc. Owing to the spherical aberration, secondary maxima are obtained in the intensity profile 29 shortly before the sharp drop. At a laser power of 500 mW, the maximum intensity of the intensity profile 29 is approximately 6 mW/cm$^2$.

FIGS. 5 to 8 show a development of the frontal or axial microdiffuser, the outlet aperture 1 being surrounded by air nozzles 30 from which air is discharged to blow away interfering body fluids. The air nozzles 30 are supplied with air by way of air ducts 31 which are shown in FIGS. 6 and 8. The air ducts 31 surround a rectangular tube 32 having a cylindrical inner cavity 33 for accommodating the microlenses 14 and 15, the brass ring 18 and the brass tube 21 in the manner already known from FIG. 1. The optical fibre 8 extends through a guide member 34, the structure of which is shown in FIGS. 5, 6 and 7.

The arrangement described so far is surrounded by an air-supply tube or outer tube 35 which is shown in FIGS. 5, 6, 7 and 8. On the left side of FIGS. 5 and 7 can be seen a PTFE tube 36 having an inside diameter of 2.5 mm and a wall thickness of 0.25 mm. By way of the PTFE tube 36, flushing air passes through a first air-feed duct 37 and a second air-feed duct 38, which are shown in FIGS. 6 and 7, into the air ducts 31.

As can be seen in FIG. 7, the guide member 34 is substantially in the form of a round rod out of which two axially extending grooves have been cut to form the air-feed ducts 37 and 38. A duct 39 in the guide member 34 has the same task as the duct 5 in the embodiment of the axial or frontal microdiffuser shown in FIG. 1.

In the embodiment shown in FIGS. 5 and 6, the pencil of rays 13 emerging from the end face 9 has the same optical properties and is subject to the same optical conditions as in the case of the embodiment according to FIG. 1. For that reason, the cone 2 of emerging light has, as in the case of the embodiment according to FIG. 1, a cone angle of 60 degrees and permits the production of a homogeneous sharp-edged illuminated light disc on a tumour tissue for the purpose of photodynamic therapy.

What is claimed is:

1. A fibre-optic apparatus for the photodynamic treatment of tumours in a patient, which apparatus has an optical fibre connected to a laser for conveying light to a site of the tumour in a patient, wherein first and second lenses comprising a pair of lenses (14, 15) which are similar plano-convex microlenses (14, 15), each microlens having a planar side and a convex side; a focal length which locates a focal point relative to the lens; a central ray axis; and a diameter the focal length of which is smaller than the diameter thereof, said microlenses being arranged such that the convex sides (19, 20) thereof are facing each other and which are at a distance from one another that is smaller than the focal length of the microlenses (14, 15), and including means for locating said microlenses coaxially with respect to a light (13)-emitting end face (9) of the fibre (8) and are so adjusted and have a spherical aberration such that edge rays (23) having an angle of divergence (β) of a divergent pencil of light rays (23) emerging from the end face (9) of the fibre (8) are so greatly refracted by the first lens (14) of the lens pair, owing to the spherical aberration of said first lens (14), that, after traversing radially the central ray axis of the pair of lenses (14, 15) before the focal point (24'), said edge rays enter the convex side (20) of the second lens (15) of the lens pair (14, 15) at a site (25) lying diametrically opposite a site of emergence (26) from the convex side (19) of the first lens (14), as a result of which the angle of divergence (β) of the edge rays (23) is reduced.

2. An apparatus according to claim 1, wherein the end face (9) of the fibre (8) is arranged at a distance from the planar side (41) of the first lens (14) that is a multiple of the focal length thereof.

3. An apparatus according to claim 1, wherein the optical fibre (8) has a core diameter of 200 μm, a numerical aperture of 0.21; and is a distance of 3.2 mm from the first plano-convex microlens (14) the lenses (14, 15) being separated by a distance of 0.7 mm the diameter thereof being 1.5 mm and the focal length thereof being 1 mm.

4. An apparatus according to claim 1, wherein the lenses are made of flint glass having a refractive index of 1.876 at 630 nm.

5. An apparatus according to claim 1, wherein the apparatus contains a lens tube having a front and rear end and the pair of lenses consisting of the microlenses (14, 15) is arranged near the front end of a lens tube (3) in the rear end of which the optical fibre (8) is secured.

6. An apparatus according to claim 5, wherein the lens tube (3, 32) is surrounded by an air-supply tube (35) having a front end and between the lens tube (3, 32) and the air-supply tube (35) there are arranged air ducts (31, 37, 38) that open into air nozzles (30) formed on the front end (1) of the air-supply tube (35).

* * * * *